United States Patent
Wang et al.

(10) Patent No.: US 8,342,469 B2
(45) Date of Patent: Jan. 1, 2013

(54) POSITIONING SYSTEM FOR A SUSPENDED MEDICAL DEVICE

(75) Inventors: Zhenggang Wang, Shenzhen (CN); Shanzhi Huang, Shenzhen (CN); Yuan Wang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 372 days.

(21) Appl. No.: 12/883,007

(22) Filed: Sep. 15, 2010

(65) Prior Publication Data
US 2011/0073736 A1    Mar. 31, 2011

(30) Foreign Application Priority Data
Sep. 30, 2009   (CN) .......................... 2009 1 0190544

(51) Int. Cl.
*A47H 1/10*         (2006.01)
(52) U.S. Cl. ......... 248/323; 248/343; 248/611; 378/193
(58) Field of Classification Search .................. 248/343, 248/611, 581, 610, 317, 323; 378/193, 197
See application file for complete search history.

(56) References Cited

U.S. PATENT DOCUMENTS

| 2,597,875 | A | * | 5/1952 | Kruger .................... 362/217.05 |
| 3,556,523 | A | * | 1/1971 | Hooker ........................ 473/443 |
| 4,254,341 | A | | 3/1981 | Herr et al. |
| 5,037,059 | A | | 8/1991 | Asano et al. |
| 5,048,070 | A | * | 9/1991 | Maehama et al. ............. 378/197 |
| 5,148,467 | A | * | 9/1992 | Sato et al. ..................... 378/197 |
| 7,191,992 | B2 | * | 3/2007 | Wagner et al. ................ 248/317 |

FOREIGN PATENT DOCUMENTS

| CN | 2705120 Y | 6/2005 |
| CN | 201111410 Y | 9/2008 |
| CN | 201333043 Y | 10/2009 |
| JP | 2004075204 A | 3/2004 |

* cited by examiner

*Primary Examiner* — Bradley Duckworth
(74) *Attorney, Agent, or Firm* — Kory D. Christensen; Stoel Rives LLP

(57) ABSTRACT

A positioning system for a suspended medical device includes a positioning adjustment block fixed on a ceiling rail, a latch assembly, and a positioning assembly fixed on a trolley. The latch assembly is in a snap fit with the positioning adjustment block, and the latch assembly is connected to the positioning assembly through buffer springs.

10 Claims, 3 Drawing Sheets

POSITIONING SYSTEM FOR A SUSPENDED MEDICAL DEVICE

CROSS-REFERENCE TO RELATED APPLICATIONS

This application claims the benefit of Chinese Patent Application No. 200910190544.8 filed Sep. 30, 2009, which is incorporated herein by reference in its entirety.

TECHNICAL FIELD

The present disclosure relates to positioning systems for medical devices.

DETAILED DESCRIPTION

Figure 1:
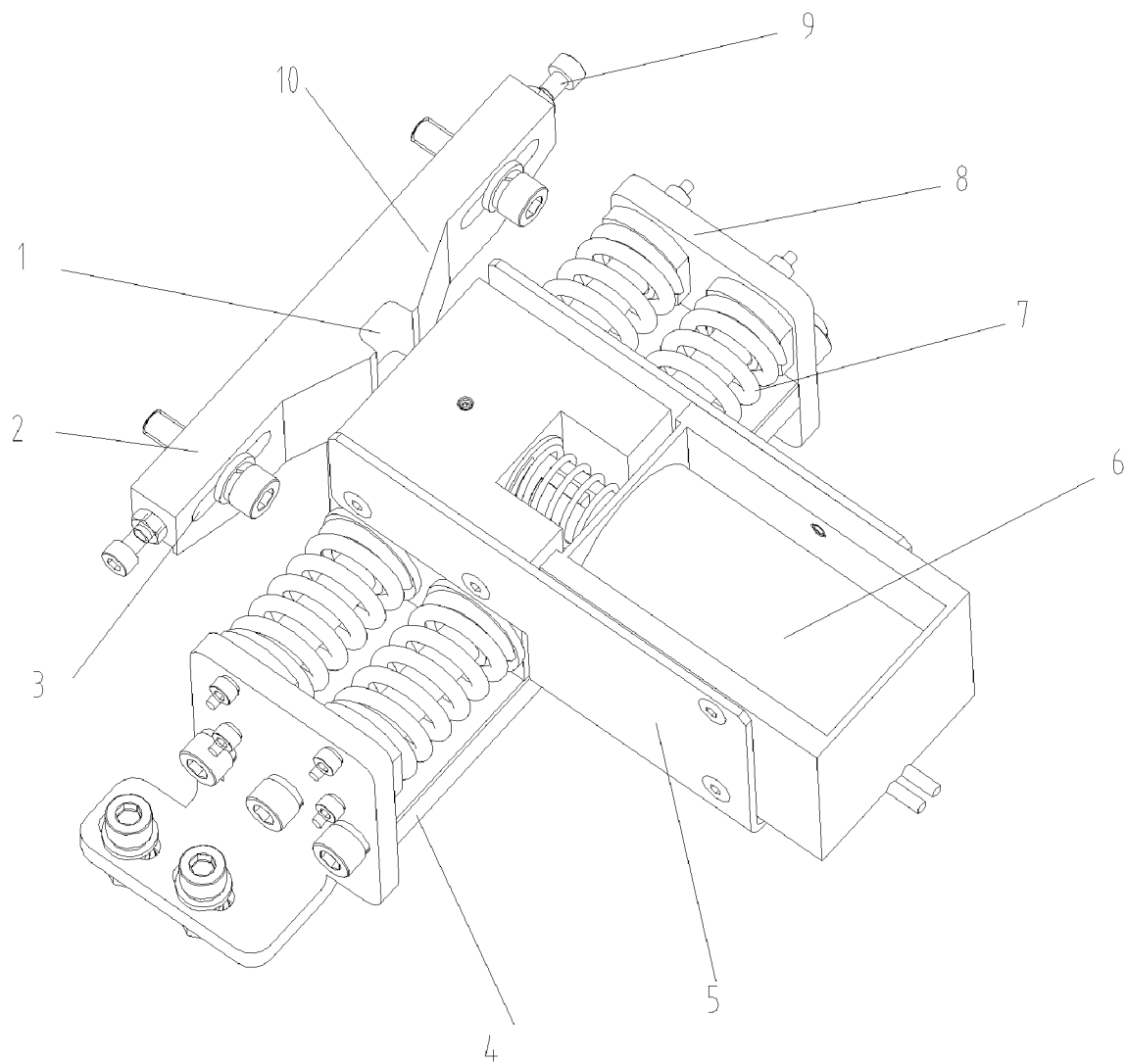
FIG. 1 is a top view of a positioning system.

In suspended medical X-ray photography systems, an X-ray generation device is typically positioned at a chest position and an under-bed position in one of two ways. First, a sensor may be used to sense set chest and under-bed positions, and then a braking device is used for trolley positioning. Alternatively, a latch structure may be used to perform trolley positioning, in which a latch stopper is mounted at a location where a fixed object needs to be positioned, and a moving object is positioned by snapping a latch in the latch stopper when the moving object moves to the corresponding position.

The positioning method using the sensor can avoid a complex mechanical structure. However, due to limited precision of the sensor and delay or overshoot in controlling the braking device, this method has a low positioning precision, and the alignment is often inaccurate. Although the positioning by using the latch structure can increase accuracy, in currently employed methods, due to heavy trolley and loaded devices, mechanical positioning has a great impact on the system, causes much vibration, which may damage the mechanical structure and interfere with a doctor's operation of the system.

In order to solve the above technical problems, the present disclosure is directed to a positioning system for a suspended medical device, which may include a positioning adjustment block fixedly connected to a ceiling rail, a latch assembly, and a positioning assembly fixedly connected to a trolley. The latch assembly may be in a snap fit with the positioning adjustment block. The positioning system may further include a buffer device, and the latch assembly may be connected to the positioning assembly through the buffer device.

In one embodiment, the buffer device may comprise buffer springs. The latch assembly may be connected to the positioning assembly through two buffer springs on two sides.

The positioning assembly may include positioning side plates and a positioning bottom plate. The positioning side plates may be fixedly connected to the positioning bottom plate, the positioning bottom plate may support the latch assembly, and the positioning side plates may be connected to the buffer springs and the trolley.

The positioning adjustment block may include a boss, and a slot mated with the latch assembly may be disposed in the boss. The positioning adjustment block may include a positioning adjustment block body, fixing screws, backing-up screws, and waist-shaped holes. The fixing screws may fix the positioning adjustment block body on the ceiling rail through the waist-shaped holes, and the backing-up screws may press against the fixing screws.

The latch assembly may include an electromagnet, a latch, and a compression spring. A moving iron core in the electromagnet may be fixedly connected to the latch, such that when the electromagnet is powered on, the moving iron core pulls the latch back to compress the compression spring, and when the electromagnet is powered off, the compression spring pushes the latch out by an elastic force.

The positioning assembly may include positioning guide shafts fixed on the positioning side plates. The latch assembly may include a positioning slide block, and the positioning slide block may slide on the positioning guide shafts. In one embodiment, the buffer springs are sleeved on the positioning guide shafts.

The present disclosure further provides a suspended medical device, which may include a ceiling rail, a trolley, and the above-described positioning device.

By using buffer springs, when the latch is snapped in the slot of the positioning adjustment block, the entire system is positioned stably and accurately due to the buffering effect of the buffer springs on both the positioning adjustment block and the trolley, thereby facilitating a doctor's operation of the system.

Referring to FIG. 1, a positioning system for a suspended medical device may includes a positioning adjustment block fixed on a ceiling rail, a positioning assembly fixed on a trolley, a buffer device, and a latch assembly connected to the positioning assembly through the buffer device. The buffer device may include buffer springs 7. The positioning assembly may include a positioning bottom plate 4, positioning side plates 8, positioning guide shaft seats 15, and positioning guide shafts 12. The latch assembly may include an electromagnet support 5, an electromagnet 6, a latch 11, a positioning slide block 14, and a compression spring 13.

The positioning adjustment block may include a positioning slot 1, a positioning adjustment block body 2, a boss 10 capable of compressing the latch in two directions, waist-shaped holes 3, fixing screws, and backing-up screws 9. In one embodiment, the fixing screws fix the positioning adjustment block body 2 on the ceiling rail through the waist-shaped holes 3, and the backing-up screws 9 press against the fixing screws.

As shown in FIG. 1, the positioning adjustment block body 2 may be fixed on the ceiling rail by the fixing screws passing through the left and right waist-shaped holes 3, and the mounting position thereof can be adjusted in a certain range through the waist-shaped holes 3. Since the structure will be subjected to impact, the backing-up screws 9 are added on the left and right sides, for pressing against the fixing screws to fix the positioning adjustment block 2 and to prevent loosening thereof under impact. In the illustrated embodiment, the positioning slot 1 in the middle and the latch 11 in the latch assembly in FIG. 2 are in a snap fit and are together used for mechanical positioning.

Figure 2:
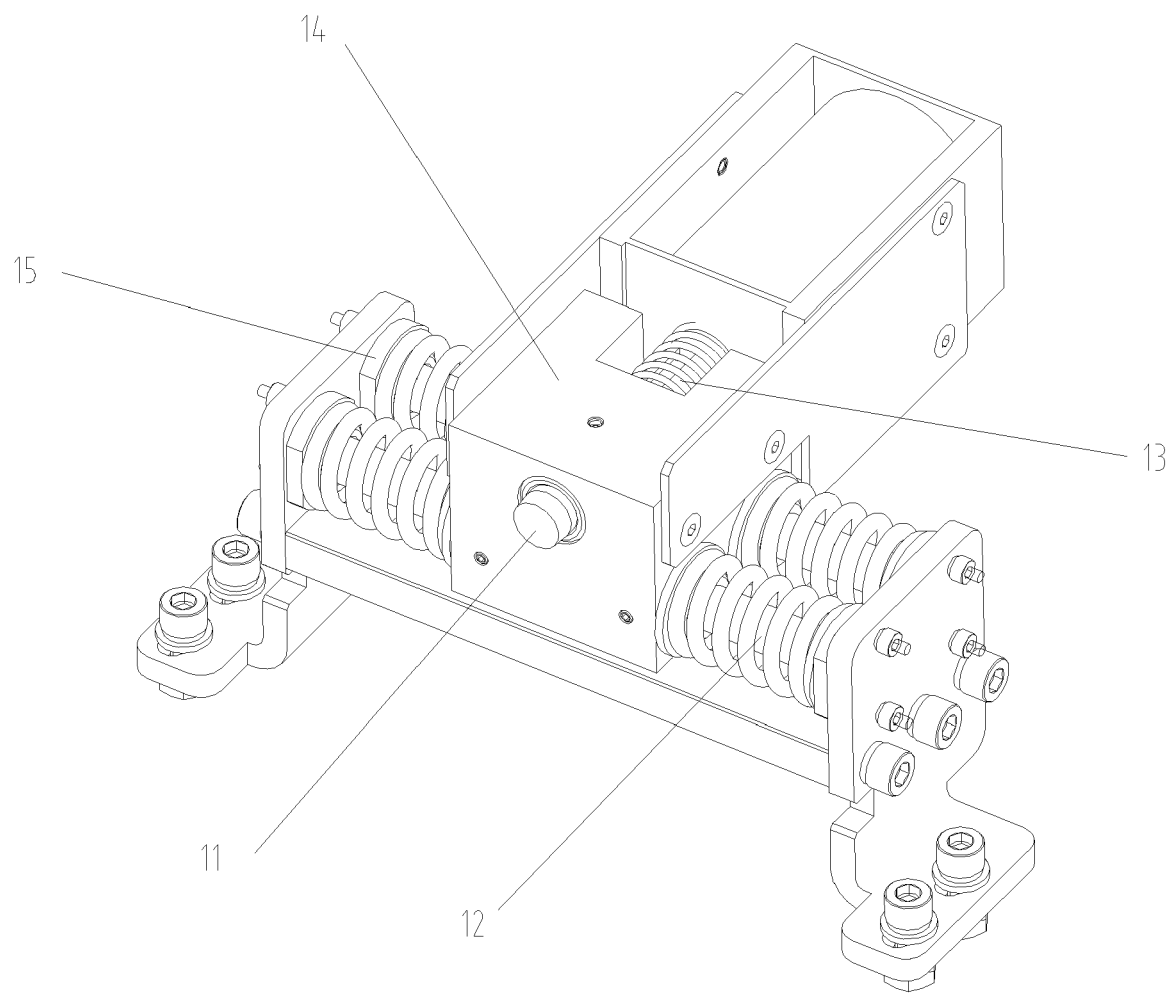
FIG. 2 is a front isometric view of the positioning system.
Figure 3:
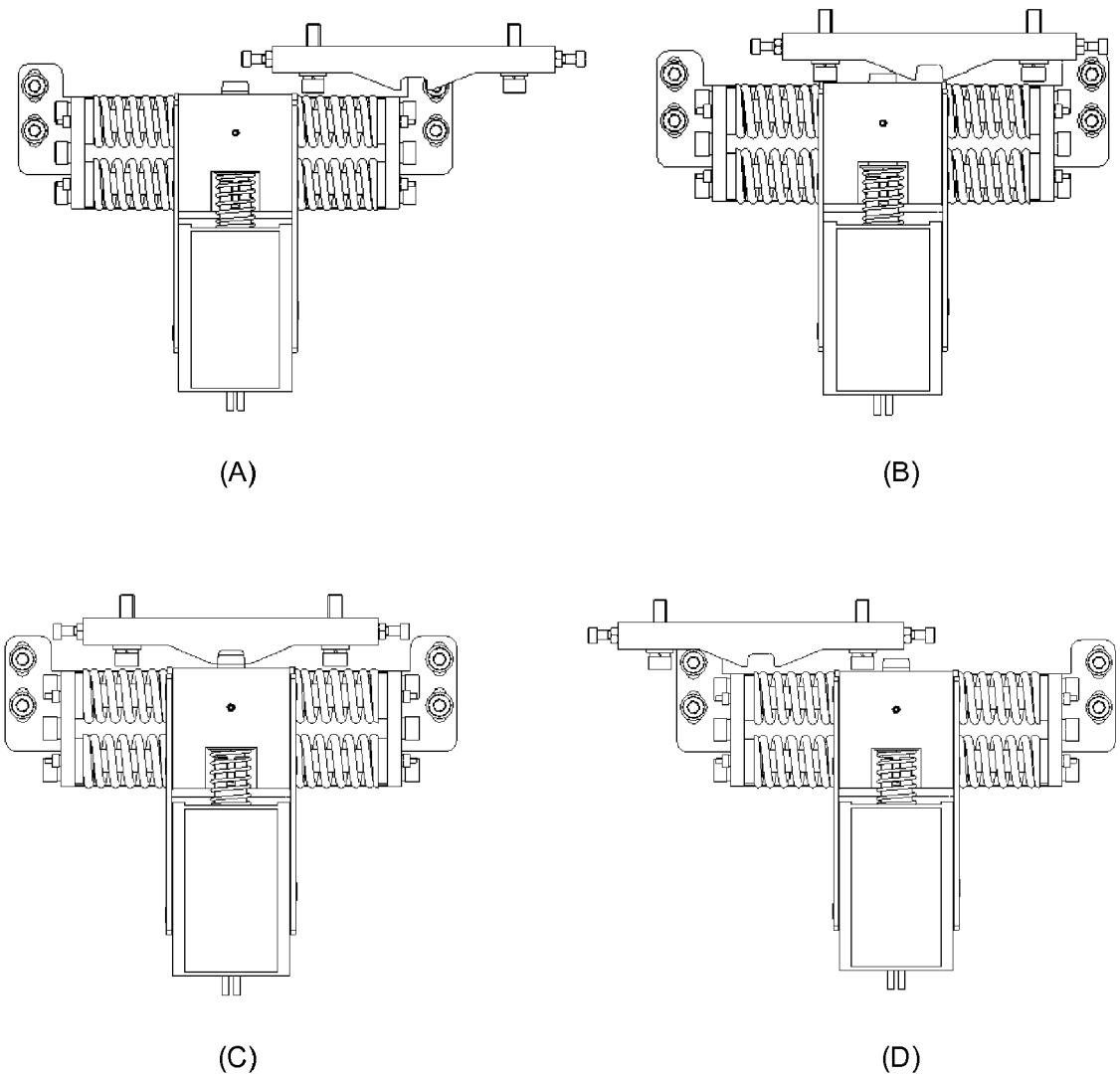
FIGS. 3(A) through 3(D) are schematic views illustrating motion of the positioning system.

As shown in FIGS. 1 and 2, the latch 11 may be riveted to a moving iron core in the electromagnet 6, the compression spring 13 may be pressed between the latch 11 and the electromagnet 6, the electromagnet 6 and the positioning slide block 14 may be connected through the electromagnet support 5 and fixed by screws, and the latch 11 may be slidable in the positioning slide block 14. When the electromagnet 6 is powered on, the moving iron core pulls the latch 11 back to compress the compression spring 13; and when the electromagnet 6 is powered off, the compression spring 13 pushes the latch 11 out by an elastic force.

The two positioning guide shafts 12 may pass through the positioning slide block 14, so that the positioning slide block 14 and the structure connected thereto are slidable left and right along the positioning guide shafts 12. The four positioning guide shaft seats 15 may be connected to the two positioning side plates 8, and the four buffer springs 7 may be mounted between the four positioning guide shaft seats 15 and the positioning slide block 14. In one embodiment, the two positioning side plates 8 on the left and right sides are connected to the positioning bottom plate 4 to form a support structure.

The positioning assembly may be fixed on the trolley through mounting holes on the two positioning side plates 8 on the left and right sides. Different buffer distances and time can be obtained by designing buffer springs 7 of different specifications according to the overall energy of motion of the machine, so as to meet use requirements in different occasions. The buffer springs 7 may be pre-compressed by a distance when being mounted, so as to enhance the buffering effect of the buffer structure.

The process of motion buffering of the positioning system is described as follows. As shown in FIGS. 3A, 3B, 3C, and 3D, the latch assembly moves with the trolley towards a position determined by the positioning adjustment block. In one embodiment, the latch 11 is compressed when contacting the boss 10. When the latch assembly moves to the position of the positioning slot 1, the latch 11 is pushed into the positioning slot 1 under the effect of the compression spring 13 so as to position the entire system, the buffer springs 7 have a buffering effect, and the moving object stops at the position determined by the positioning adjustment block under the spring force. Afterwards, to continue to move, the moving iron core of the electromagnet 6 may drive and pull the latch 11 out of the positioning slot 1, and then the trolley may continue to move.

Various alterations may be made within the scope of the present disclosure. For example, the number of the buffer springs may be increased or decreased, the buffer springs may not be sleeved on the positioning guide shafts, and/or the buffer springs may be disposed on only one side. In one embodiment, buffering may be realized through energy absorbing and buffer structures in other forms. For example, cylinders, blade springs, or a high elastic material, which is easy to recover and can maintain its shape, such as rubber, may be used. In certain configurations, slide guide structures in other forms, e.g., guide rails, may be used to replace the guide shafts. Likewise, the insertion and extraction of the latch may be realized in other forms, such as being controlled by a mechanical transmission mechanism. The latch 11 may also be fixedly connected to the iron core in the electromagnet 6 by soldering or the like.

The present disclosure may be applied in a suspended medical X-ray photography system, a medical tower crane system, or other suitable systems.

The present disclosure further provides a suspended medical device, which includes a ceiling rail, a trolley, a latch assembly, a positioning adjustment block fixedly connected to the rail, and a positioning assembly fixedly connected to the trolley. The latch assembly may be in a snap fit with the positioning adjustment block. The device further may include a buffer device. The latch assembly may be connected to the positioning assembly through the buffer device. The trolley may be used, for example, to carry main components of an X-ray photography system.

It will be understood by those having skill in the art that many changes may be made to the details of the above-described embodiments without departing from the underlying principles of the invention. The scope of the present invention should, therefore, be determined only by the following claims.

What is claimed is:

1. A positioning system for a suspended medical device, comprising:
    a positioning adjustment block fixedly connected to a ceiling rail;
    a latch assembly;
    a buffer device; and
    a positioning assembly fixedly connected to a trolley, wherein the latch assembly is in a snap fit with the positioning adjustment block, and wherein the latch assembly is connected to the positioning assembly through the buffer device.

2. The positioning system of claim 1, wherein the buffer device comprises buffer springs.

3. The positioning system of claim 2, wherein the latch assembly is connected to the positioning assembly through two buffer springs on two sides.

4. The positioning system of claim 2, wherein the positioning assembly comprises positioning side plates and a positioning bottom plate, wherein the positioning side plates are fixedly connected to the positioning bottom plate, wherein the positioning bottom plate supports the latch assembly, and wherein the positioning side plates are connected to the buffer springs and the trolley.

5. The positioning system of claim 1, wherein the positioning adjustment block comprises a boss, and wherein a slot mated with the latch assembly is disposed in the boss.

6. The positioning system of claim 1, wherein the positioning adjustment block comprises a positioning adjustment block body, fixing screws, backing-up screws, and waist-shaped holes; wherein the fixing screws fix the positioning adjustment block body on the ceiling rail through the waist-shaped holes; and wherein the backing-up screws press against the fixing screws.

7. The positioning system of claim 1, wherein the latch assembly comprises an electromagnet, a latch, and a compression spring; wherein a moving iron core in the electromagnet is fixedly connected to the latch, such that when the electromagnet is powered on, the moving iron core pulls the latch back to compress the compression spring, and when the electromagnet is powered off, the compression spring pushes the latch out by an elastic force.

8. The positioning system of claim 4, wherein the positioning assembly comprises positioning guide shafts fixed on the positioning side plates; wherein the latch assembly comprises a positioning slide block; and wherein the positioning slide block slides on the positioning guide shafts.

9. The positioning system of claim 8, wherein the buffer springs are sleeved on the positioning guide shafts.

10. A suspended medical device, comprising:
    a ceiling rail,
    a trolley, and
    a positioning system including:
        a positioning adjustment block fixedly connected to a ceiling rail;
        a latch assembly;
        a buffer device; and
        a positioning assembly fixedly connected to a trolley, wherein the latch assembly is in a snap fit with the positioning adjustment block, and wherein the latch assembly is connected to the positioning assembly through the buffer device.

* * * * *